(12) United States Patent
Du et al.

(10) Patent No.: US 10,197,483 B2
(45) Date of Patent: Feb. 5, 2019

(54) TESTER ASSEMBLED BY MULTIPLE SETS OF MECHANISMS FOR SHEAR STRENGTH-SCALE EFFECT OF ROCK JOINT

(71) Applicant: SHAOXING UNIVERSITY, Shaoxing, Zhejiang Province (CN)

(72) Inventors: Shigui Du, Shaoxing (CN); Yuanjun Lv, Shaoxing (CN); Zhanyou Luo, Shaoxing (CN); Jintao Lai, Shaoxing (CN); Man Huang, Shaoxing (CN); Chengrong Ma, Shaoxing (CN); Bo Li, Shaoxing (CN); Rui Yong, Shaoxing (CN); Yunjin Hu, Shaoxing (CN); Zhen Zhong, Shaoxing (CN); Zhihai He, Shaoxing (CN)

(73) Assignee: SHAOXING UNIVERSITY, Shaoxing (CN)

( * ) Notice: Subject to any disclaimer, the term of this patent is extended or adjusted under 35 U.S.C. 154(b) by 77 days.

(21) Appl. No.: 15/436,517

(22) Filed: Feb. 17, 2017

(65) Prior Publication Data
US 2018/0128725 A1 May 10, 2018

(30) Foreign Application Priority Data
Nov. 7, 2016 (CN) .......................... 2016 1 0976607

(51) Int. Cl.
*G01N 3/24* (2006.01)
*G01N 3/10* (2006.01)

(52) U.S. Cl.
CPC ................. *G01N 3/24* (2013.01); *G01N 3/10* (2013.01); *G01N 2203/0003* (2013.01); *G01N 2203/0025* (2013.01); *G01N 2203/0048* (2013.01)

(58) Field of Classification Search
CPC ............. G01N 3/24; G01N 2203/0048; G01N 2203/0003; G01N 2203/0025
(Continued)

(56) References Cited

U.S. PATENT DOCUMENTS

2018/0031457 A1* 2/2018 Jiang ........................ G01N 3/24

FOREIGN PATENT DOCUMENTS

| CN | 103335895 A | * 10/2013 |
| CN | 104062189 A | * 9/2014 |

* cited by examiner

*Primary Examiner* — Jonathan Dunlap
(74) *Attorney, Agent, or Firm* — Jiwen Chen

(57) ABSTRACT

A tester assembled by multiple sets of mechanisms for shear strength-scale effect of a rock joint includes a horizontal loading mechanism, a horizontal supporting and force-measuring mechanism and a sample installation and lifting table are mounted on a platform on the bottom of a frame, the horizontal loading mechanism and the horizontal supporting and force-measuring mechanism are respectively located on two sides of the sample installation and lifting table; rock joint sample is divided into an upper portion and a lower portion by a slit, the horizontal loading mechanism is configured to load the upper portion of the multi-scale rock joint sample, and the horizontal supporting and force-measuring mechanism is configured to support the lower portion of the multi-scale rock joint sample; a vertical loading mechanism is located above the multi-scale rock joint sample, and can be mounted on the frame in a manner of being movable up and down; and the horizontal loading mechanism comprises at least two tangential actuators, and the vertical loading mechanism comprises a vertical actuator group including at least two vertical actuators. The present invention effectively meets the test requirements on the scale of the multi-scale rock joint samples under large-range loads, and is good in reliability.

14 Claims, 8 Drawing Sheets

(58) Field of Classification Search
USPC .......................................... 73/815, 841–846
See application file for complete search history.

TESTER ASSEMBLED BY MULTIPLE SETS OF MECHANISMS FOR SHEAR STRENGTH-SCALE EFFECT OF ROCK JOINT

This application claims the priority benefit of Chinese Application No. 201610976607.2 filed Nov. 7, 2016, which is hereby incorporated by reference.

TECHNICAL FIELD

The present invention relates to a tester for shear strength-scale effect of a rock joint/structural surface.

BACKGROUND OF THE INVENTION

The scale effect, which is a common feature in tests of mechanical properties of rocks, refers to a phenomenon in which a certain characteristic varies with different scales of an object. The characteristic that the mechanical properties of rocks decrease with the increase of the sample scale exists not only in the tensile, compressive, shear, elastic modulus and rheological properties of rocks, but also in the shear characteristics of rock joints. In order to study the shear strength-scale effect of a rock joint, a scale effect test system is required to complete the tests of the rock joint, and to establish direct shear tests for rock joint samples of different scales under same load stress level.

At present, among direct shear test apparatuses for the scale effect of a rock joint are, D U Shigui proposed testing machines for shear strength-scale effect of a rock joint/structural surface (CN201410149668.2) and multiple scales rocks shearing machines (CN201310273743.1). They are structurally designed in terms of mounting, transportation, parts protection, testing mechanisms, etc. of multi-scale samples. However, due to the limitation on the test load and the test range of each transducer, each actuator and controller, the requirements on accuracy within a large range of loads cannot be met well by only one loading system. It is very important to develop a direct shear tester assembled by multiple sets of mechanisms for shear strength-scale effect of a rock joint, which is applicable to a large range of loads and provides high accuracy testing results.

SUMMARY OF THE INVENTION

In order to overcome the shortcomings that the existing direct shear apparatuses cannot meet the test requirements on shear strength of multi-scale samples and are lower in reliability, the present invention provides a tester for scale effect of a rock joint, which effectively meets the test requirements on the scale of multi-scale rock joint samples under large-range loads, and is good in reliability.

To solve the technical problems, the present invention employs the following technical solution.

A tester assembled by multiple sets of mechanisms for shear strength-scale effect of a rock joint is provided, comprising a frame, a horizontal loading mechanism, a horizontal supporting and force-measuring mechanism, a vertical loading mechanism, and a sample installation and lifting table configured to place different size sample of a rock joint, wherein the horizontal loading mechanism, the horizontal supporting and force-measuring mechanism and the sample installation and lifting table are mounted on a platform on the bottom of the frame, the horizontal loading mechanism and the horizontal supporting and force-measuring mechanism are respectively located on two sides of the sample installation and lifting table; the rock joint sample is divided into an upper portion and a lower portion by a slit, the horizontal loading mechanism is configured to load the upper portion of the multi-scale rock joint sample, and the horizontal supporting and force-measuring mechanism is configured to support the lower portion of the multi-scale rock joint sample; the vertical loading mechanism is located above the multi-scale rock joint sample, and can be mounted on the frame in a manner of being movable up and down; and the horizontal loading mechanism includes at least two tangential actuators, and the vertical loading mechanism includes a vertical actuator group comprising at least two vertical actuators.

Further, the horizontal supporting and force-measuring mechanism includes at least two force transducers which are arranged up and down.

Still further, the vertical loading mechanism comprises a movable beam, vertical actuators, a sprocket drive mechanism, a motor, a vertical force transducer, a movable joint, loading plates and guide rail blocks. Worm gears are installed on two sides of the movable beam. The outer rings of the worm gears can be rotatably sleeved inside mounting holes of the movable beam. Four upright columns of the frame pass through the worm gears and are in running fit with inner rings of the worm gears; the sprocket drive mechanism is respectively connected to the motor and a shaft end of a worm, and the worm is meshed with the worm gears, and the motor rotates to drive the worm gears to rotate so that the movable beam moves up and down along the upright columns; an actuator group, comprising 2n+1 actuators distributed symmetrically, is arranged on the movable beam, where n is a natural number; the vertical force transducer, the other end of which is connected to the movable joint, is mounted on a piston rod of each vertical actuator, and the movable joint is connected to the loading plate having a group of guide rail blocks mounted on its bottom.

Preferably, in the vertical loading mechanism, the 2n+1 vertical actuators are distributed in a shape of "-" or "X". Of course, the actuators can be distributed in other symmetrical ways, and can be distributed in other ways, for example, in an array.

Still further, the horizontal supporting and force-measuring mechanism includes a second horizontal force transducer, a horizontal supporting tip, guide rods, a first guide base, a first force transducer, a second guide base, snap rings, a supporting hydraulic cylinder, a mounting frame, guide rods, a linear bearing, a jack and a pedestal, the mounting frame is divided into three layers in vertical direction; the four guide rods, bottoms of which are mounted on the pedestal, are mounted on two sides of a bottom layer of the mounting frame through a linear bearing; and the jack, an acting end of which is connected to the bottom of the mounting frame, is mounted in the middle layer of the mounting frame.

The first force transducer is mounted in the middle layer of the mounting frame.

The supporting hydraulic cylinder is mounted in a top layer of the mounting frame; the piston rod and the horizontal supporting tip are fixed; the horizontal supporting tip, pushed by the supporting hydraulic cylinder, can be for returning a sample of the upper portion to the original position after the test; and a connecting rod is mounted at a front end of the horizontal supporting tip for mounting the second force transducer.

Preferably, the guide rods, which pass through the first guide base and the second guide base fixed on the mounting frame, are mounted on two sides of the horizontal supporting tip; and several groups of shaft shoulders which, after moving to a certain position, are sleeved to two sides of the second guide base through the two snap rings for the purpose of limiting the guide rods, are arranged on tail ends of the guide rods.

The frame includes a fixed beam, upright columns and a platform; the frame is a four-column mechanism; and the four upright columns are mounted on two sides of the platform and the fixed beam, the fixed beam is located above the upright columns, the platform is located below the upright columns, and the upright columns have trapezoidal threads on the upper half thereof.

The sample installation and lifting table includes a sample limiting seat, a sample loading plate, L-shaped plates, a sample mounting plate, tangential guide rails, a trolley, a two-stage telescopic cylinder, lifting hydraulic cylinders, a sample transmission rack and a supporting rod; the L-shaped plates are diagonally mounted on the upper and lower portions of the sample respectively, and the sample is mounted on the sample mounting plate and limited by the sample limiting seat, the tangential guide rail is mounted on the trolley, and the sample mounting plate is mounted on the tangential guide rail; the sample transmission rack is mounted on one side of the platform of the frame, the two-stage telescopic cylinder is mounted inside the platform, and the supporting tip, on which the supporting rod is mounted, is mounted on the piston rod of the two-stage telescopic cylinder; and the trolley is provided with four wheels which are fixed on a small short-range hydraulic cylinder and move along limiting grooves on two sides of the sample transmission rack, the supporting rod is connected to the trolley, and an acting end of the lifting hydraulic cylinder is located below the trolley and the sample mounting plate.

The sample installation and lifting table further comprises backing plates, backing plate thrust hydraulic cylinders, a backing plate frame, thrust bars, guide bars, a backing plate transmission rack, a lifting table, guide rods and a supporting tip; a set number of backing plates are amounted according to the scale of the sample so that kerfs of the sample are on a same level of height; the backing plate transmission rack is mounted on the other side of the platform of the frame; one backing plate lifting table, on which the backing plates are mounted, is mounted inside the backing plate transmission rack; the backing plate thrust hydraulic cylinders are respectively mounted on two sides of the other side of the platform, and the thrust bars are mounted on the piston rods of the two backing plate thrust hydraulic cylinders; the backing plate frame fixed to the thrust bars is located right above the backing plates, and the two sides of the backing plate frame are movably mounted on the guide bars of the backing plate transmission rack.

The horizontal shearing mechanism comprises a tangential motor, a screw rod, dovetail groove sliding tables, tangential actuators, a moving plate, a fixed bracket, horizontal force transducers and shearing tips; at least two tangential actuators distributed symmetrically are mounted on the moving plate; the moving plate and the fixed bracket are connected by a group of dovetail groove sliding tables; a screw rod mounting base connected to the screw rod is mounted on the bottom of the moving plate, and one end of the screw rod is connected to the tangential motor; and the horizontal force transducer, on which the shearing tips are mounted, is mounted on the piston rod of each tangential actuator.

The technical concept of the present invention is as follows: a direct shear apparatus generally comprises a vertical loading mechanism and a tangential loading mechanism, each comprising a hydraulic cylinder and a force transducer and sharing one controller. Because the hydraulic loading system and the force transducer are limited by the test load range and test precision, the coordinative control of a plurality of loading mechanisms is required to meet the loading accuracy and load requirements when the test of the load range cannot be completed by one loading mechanism. For this purpose, a group of loading mechanisms distributed symmetrically is provided in the vertical and tangential loading mechanisms, and combined control by using a plurality of loading mechanisms is utilized according to the sample scale and load requirements. Meanwhile, a sample transporting and backing plate mounting device with a very high degree of automation is used, in order to effectively enable the kerfs of the samples to reach at a same level of height, and to guarantee the high rigidity of the mounting platform during the sample loading. In order to effectively realize the accuracy of a tangential force, a supporting and force measuring mechanism is used to select, according to different loads, a force transducer not to be used.

The present invention has the following beneficial effects: first, it effectively realizes direct shear tests at a same accuracy under large-range loads, and is good in reliability; and second, it is applicable to tests of multi-scale rock joint samples of different scales and specifications.

DETAILED DESCRIPTION OF THE INVENTION

Figure 1:
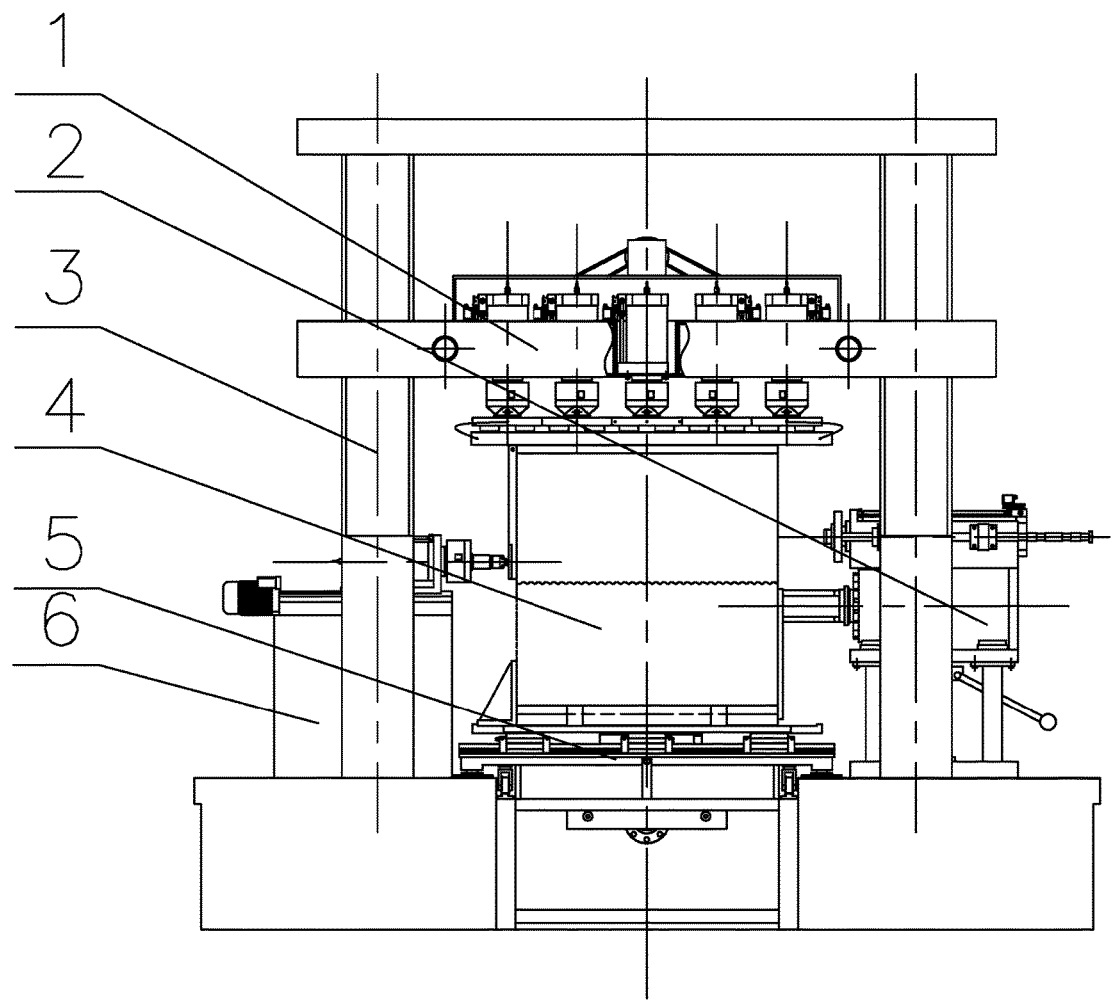
FIG. 1 is a front view of a tester assembled by multiple sets of mechanisms for shear strength-scale effect of a rock joint which is a big rock joint sample.
Figure 2:
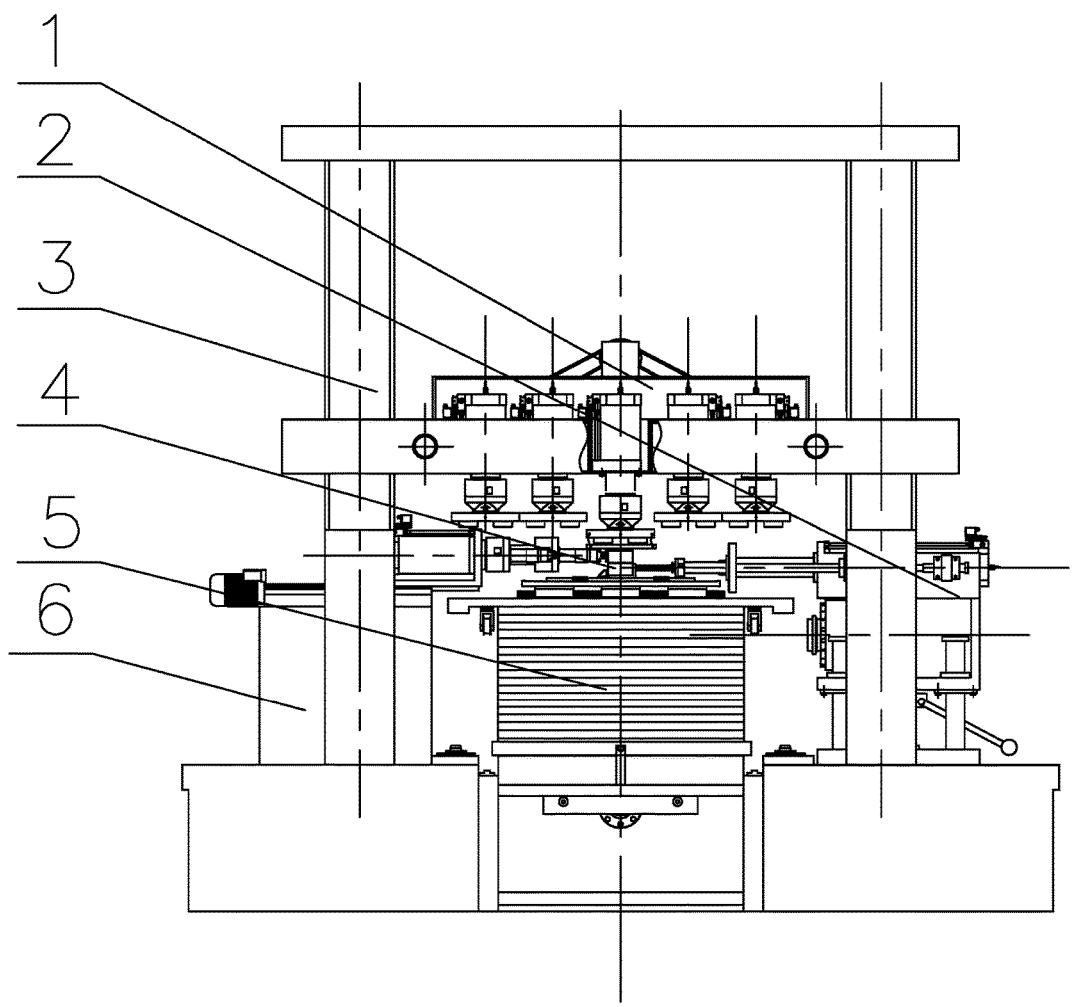
FIG. 2 is a front view of the tester assembled by multiple sets of mechanisms for shear strength-scale effect of a rock joint which is a small rock joint sample.
Figure 3:
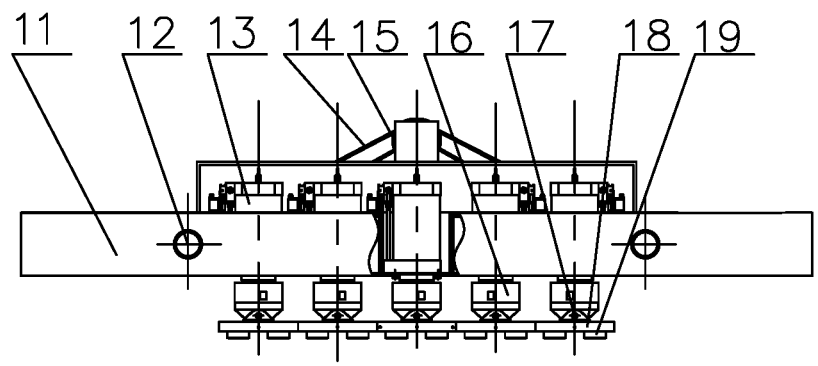
FIG. 3 is a front view of a vertical loading mechanism.
Figure 4:
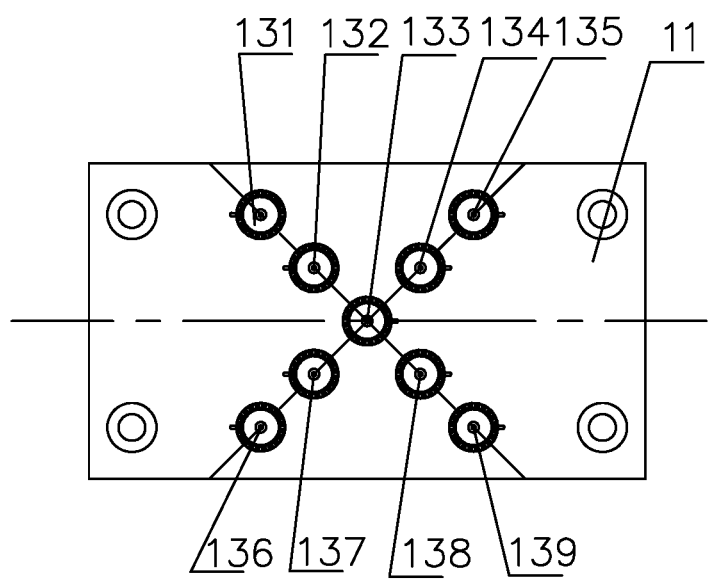
FIG. 4 is a top view of mounting positions of actuators of the vertical loading mechanism.
Figure 5:
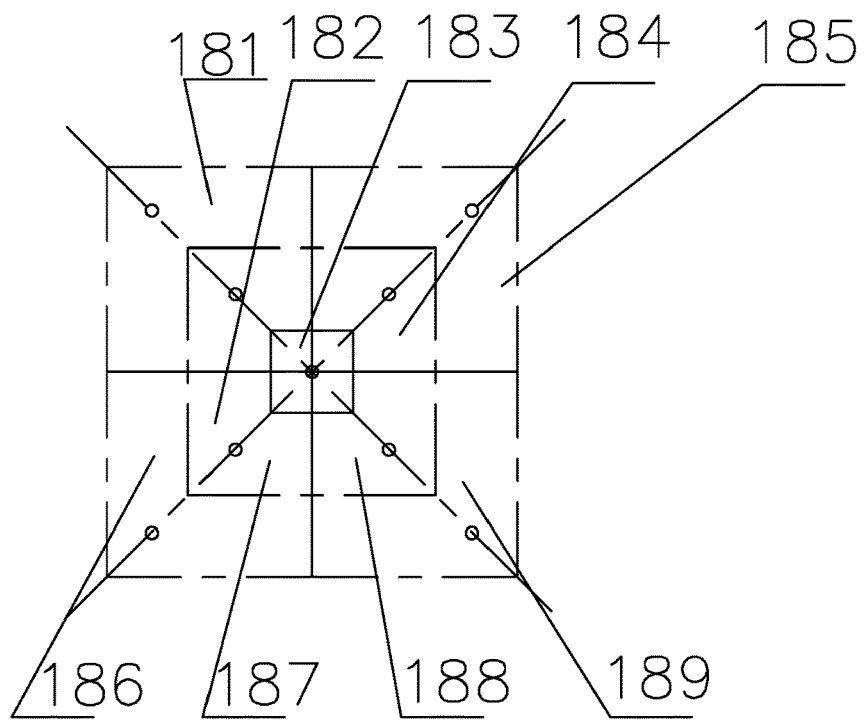
FIG. 5 is a top view showing a corresponding relationship between the actuators of the vertical loading mechanism, when in their mounting positions, and loading plates.
Figure 6:
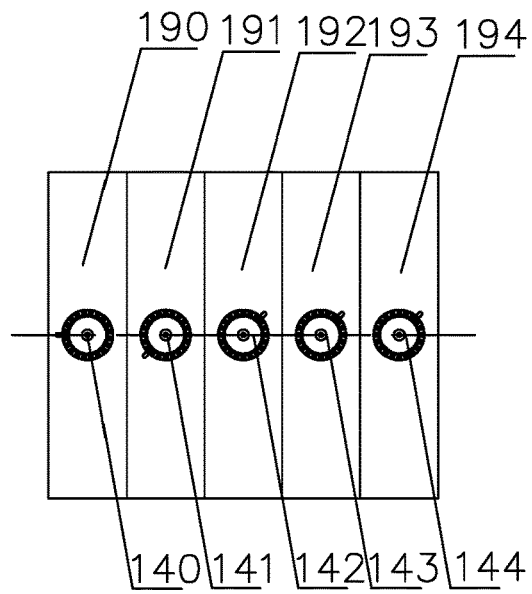
FIG. 6 is a top view showing mounting positions of actuators and loading plates of another vertical loading mechanism.
Figure 7:
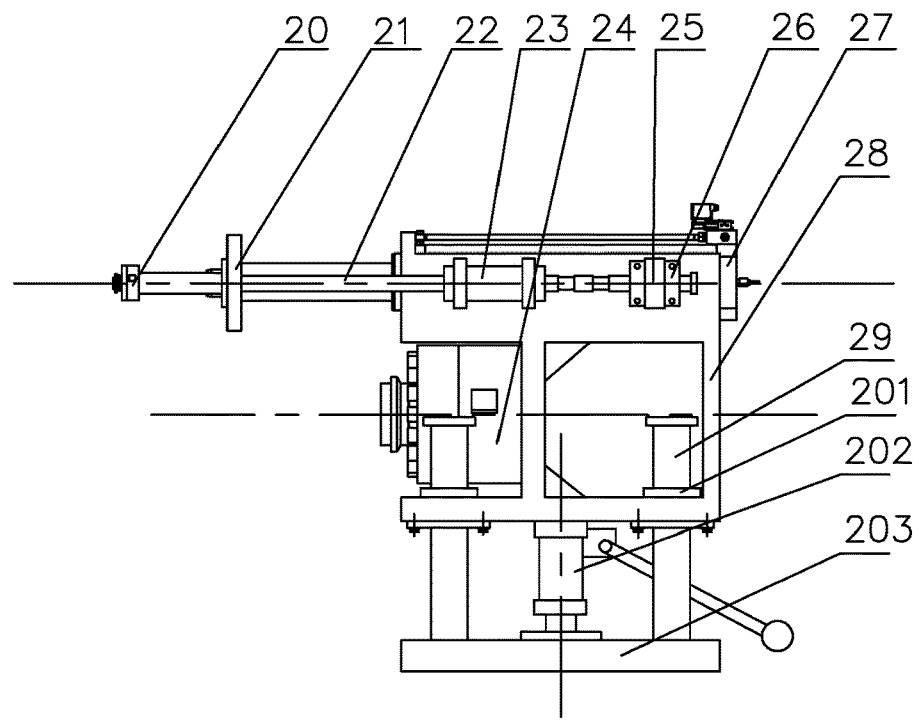
FIG. 7 is a front view of a horizontal supporting and force-measuring mechanism.
Figure 8:
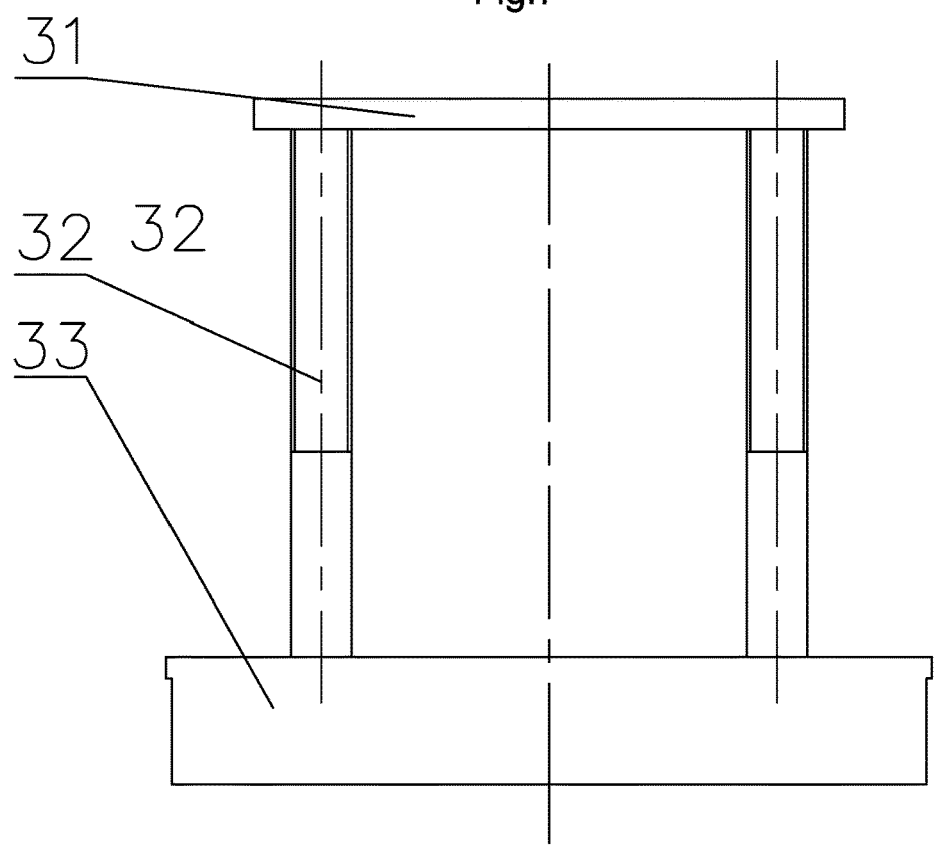
FIG. 8 is a front view of a frame.

The present invention will be further described with reference to the accompanying drawings.

With reference to FIG. 1 to FIG. 13, a tester assembled by multiple sets of mechanisms for shear strength-scale effect of a rock joint is provided, including a frame 3, a horizontal loading mechanism 6, a horizontal supporting and force-measuring mechanism 2, a vertical loading mechanism 1, and a sample installation and lifting table 5. The frame 3 is a four-column structure. The horizontal loading mechanism 6, the horizontal supporting and force-measuring mechanism 2 and the sample installation and lifting table 5 are mounted on a platform 33 on the bottom of the frame 3. The horizontal loading mechanism 6 and the horizontal supporting and force-measuring mechanism 2 are respectively located on two sides of the sample installation and lifting table 5 and on two sides of the platform 33 on the bottom of the frame 3. A multi-scale rock joint sample 4 is mounted on the sample installation and lifting table 5. The horizontal loading mechanism 6 is configured to load the upper portion of the multi-scale rock joint sample 4, and the horizontal supporting and force-measuring mechanism 2 is configured to support the lower portion of the multi-scale rock joint sample 4. The vertical loading mechanism 1 is located above the multi-scale rock joint sample 4 and mounted on upright columns 32 of the frame 3, and can move up and down along the upright columns 32.

The vertical loading mechanism 1 mainly comprises a movable beam 11, worm gears 12, vertical actuators 13, a sprocket drive mechanism 14, a motor 15, a vertical force transducer 16, a movable joint 17, loading plates 18 and guide rail blocks 19. The worm gears 12, outer rings of which can be rotatably sleeved inside mounting holes of the movable beam 11, are provided on two sides of the movable beam 11, and four upright columns 32 of the frame 3 pass through the movable beam 11 and are in thread fit with inner rings of the worm gears 12 on the two sides. The sprocket drive mechanism 14 is respectively connected to the motor 15 and a shaft end of a worm (not shown), and the motor 15 rotates to drive the worm and the worm gears 12 to rotate so that the movable beam 11 moves up and down along the upright columns. An actuator group, comprising 2n+1 actuators 13 distributed symmetrically, is arranged on the movable beam 11. The vertical force transducer 16, the other end of which is connected to the movable joint 17, is mounted on a piston rod of each vertical actuator 13, and the movable joint 17 is connected to the loading plate 18 having a group of guide rail blocks 19 mounted on its bottom.

The symmetrically distributed 2n+1 actuators 13 arranged on the movable beam 11 of the vertical loading mechanism 1 can be distributed according to the shape of the sample, where n is a natural number. For a sample in a positive direction, an actuator 133 can be arranged in the middle of the movable beam 11, and by taking the center of the actuator as the origin, the actuators are distributed in an "X" shape. Taking 9 actuators as an example, an actuator 131, an actuator 132, an actuator 133, an actuator 138 and an actuator 139 forming a straight line, and an actuator 136, an actuator 137, an actuator 133, an actuator 134 and an actuator 135 forming a straight line are crosswise mounted by taking the actuator 133 as the origin, and the corresponding loading plates on the actuators are arranged in such that the actuator 131 is matched with the loading plate 181, the actuator 132 is matched with the loading plate 182, the actuator 133 is matched with the loading plate 183, the actuator 134 is matched with the loading plate 184, the actuator 135 is matched with the loading plate 185, the actuator 136 is matched with the loading plate 186, the actuator 137 is matched with the loading plate 187, the actuator 138 is matched with the loading plate 188, and the actuator 139 is matched with the loading plate 189.

The symmetrically distributed 2n+1 actuators 13 arranged on the movable beam 11 of the vertical loading mechanism 1 can also be distributed linearly, where n is a natural number. For example, an actuator 140, an actuator 141, an actuator 142 an actuator 143 and an actuator 144 are linearly mounted in a row on the moving beam 11, and the corresponding loading plates are a loading plate 190, a loading plate 191, loading plate 192, a loading plate 193 and a loading plate 194. Of course, the actuators can be distributed in other symmetrical ways. Of course, the actuators can be distributed in other ways, for example, in an array.

The horizontal supporting and force-measuring mechanism 2 mainly comprises a second horizontal force transducer 20, a horizontal supporting tip 21, guide rods 22, a first guide base 23, a first force transducer 24, a second guide base 25, snap rings 26, a supporting hydraulic cylinder 27, a mounting frame 28, guide rods 29, a linear bearing 201, a jack 202 and a pedestal 203. The mounting frame 28 is divided into three layers in vertical direction. Four guide rods 29, bottoms of which are mounted on the pedestal 203, are mounted on two sides of a bottom layer of the mounting frame 28 through a linear bearing 201, and the jack 30 is mounted in the middle layer of the mounting frame, and the mounting frame 28 can move up and down along the four guide rods 29 through the jack 30. The first force transducer 24 is mounted in the middle layer of the mounting frame 28. A supporting hydraulic cylinder 27 is mounted in the top layer of the mounting frame 28. The piston rod and the horizontal supporting tip 21 are fixed. The horizontal supporting tip 21, pushed by the supporting hydraulic cylinder 27, can be for returning a sample of the upper portion to the original position after the test. Meanwhile, a connecting rod is mounted at a front end of the horizontal supporting tip 21 for mounting the second force transducer 20. The guide rods 22, which pass through the first guide base 23 and the second guide base 25 fixed on the mounting frame 28, are mounted on two sides of the horizontal supporting tip 21. Several groups of shaft shoulders which, after moving to a certain position, are sleeved to two sides of the second guide base 25 through the two snap rings 26 for the purpose of limiting the guide rods 22, are arranged on tail ends of the guide rods 22.

The frame 3 includes a cross beam 31, upright columns 32 and a platform 33. The frame 3 is a four-column mechanism. Four upright columns 32 are mounted on two sides of the platform 33 and the cross beam 31, the cross beam 31 is located above the upright columns 32, the platform 33 is located below the upright columns 32, and the upright columns 32 have trapezoidal threads on the upper half thereof.

The sample installation and lifting table 5 includes a sample limiting seat 50, a sample loading plate 51, L-shaped plates 52, a sample mounting plate 53, tangential guide rails 54, a trolley 55, backing plates 56, a two-stage telescopic cylinder 57, lifting hydraulic cylinders 58, a sample transmission rack 59, a supporting rod 70, a limiting rod 71, a displacement transducer 72, backing plate thrust hydraulic cylinders 73, a backing plate frame 74, thrust bars 75, guide bars 76, a backing plate transmission rack 77, a backing plate lifting table 78, guide rods 79 and a supporting tip 80. The L-shaped plates 52 are diagonally mounted on the upper and lower portions of the sample respectively, and the sample is mounted on the sample mounting plate 53 and limited by the sample limiting seat 50. A certain number of tangential guide rails 54 are mounted on the trolley 55, and the sample mounting plate 53 is mounted on the tangential guide rails 54. A set number of backing plates 56 are amounted according to the scale of the sample so that kerfs of the sample 4 are on a same level of height. The sample transmission rack 59 is mounted on one side of the platform 33, the two-stage telescopic cylinder 57 is mounted inside the platform 33, and the supporting tip 80, on which the supporting rod 70 is mounted, is mounted on the piston rod of the two-stage telescopic cylinder 57. The trolley 55 is provided with four wheels which are fixed on a small short-range hydraulic cylinder and move along limiting grooves on the two sides of the sample transmission rack 59, the supporting rod 70 is connected to the trolley 55 so as to push the trolley 55 to move under the action of the two-stage telescopic cylinder 57. The lifting hydraulic cylinder 58 can lift up the trolley 55 and the sample thereon. The backing plate transmission rack 77 is mounted on the other side of the platform 33. One backing plate lifting table 78, on which the backing plates 56 are mounted, is mounted inside the backing plate transmission rack 77. The backing plate thrust hydraulic cylinders 73 are respectively mounted on two sides of the other side of the platform 33, and the thrust bars 75 are mounted on the piston rods of the two backing plate thrust hydraulic cylinders 73. The backing plate frame 74 fixed to the thrust bars 75 is located right above the backing plates 56, and the two sides of the backing plate frame 74 can move along the guide bars 76 fixed on the backing plate transmission rack 77.

The horizontal shearing mechanism mainly comprises a tangential motor 61, a screw rod 62, dovetail groove sliding tables 63, tangential actuators 64, a moving plate 65, a fixed bracket 66, horizontal force transducers 67 and shearing tips 68. A group of the tangential actuators 64 distributed symmetrically are mounted on the moving plate 65. The moving plate 65 and the fixed bracket 66 are connected by a group of dovetail groove sliding tables 63. A screw rod mounting base connected to the screw rod 62 is mounted on the bottom of the moving plate 65, and one end of the screw rod 62 is connected to the motor 61. The motor 61 rotates to drive the moving plate 65 to move left and right. The horizontal force transducer 67, on which the shearing tips 68 are mounted, is mounted on the piston rod of each tangential actuator 64.

The working process of this embodiment is as follows.

Figure 9:
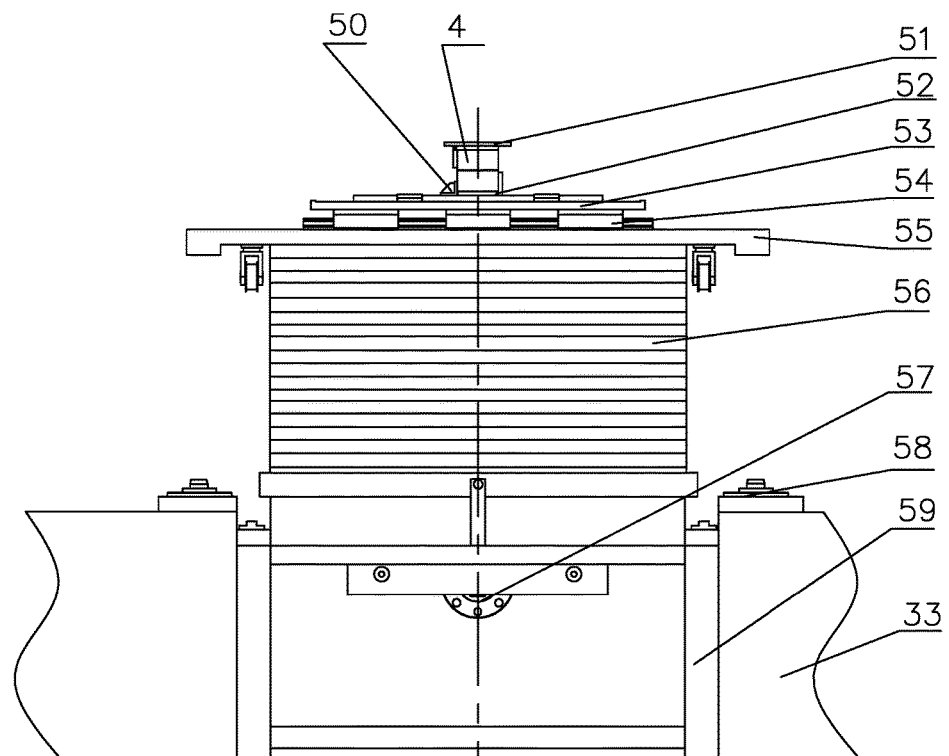
FIG. 9 is a front view of a sample installation and lifting table.
Figure 10:
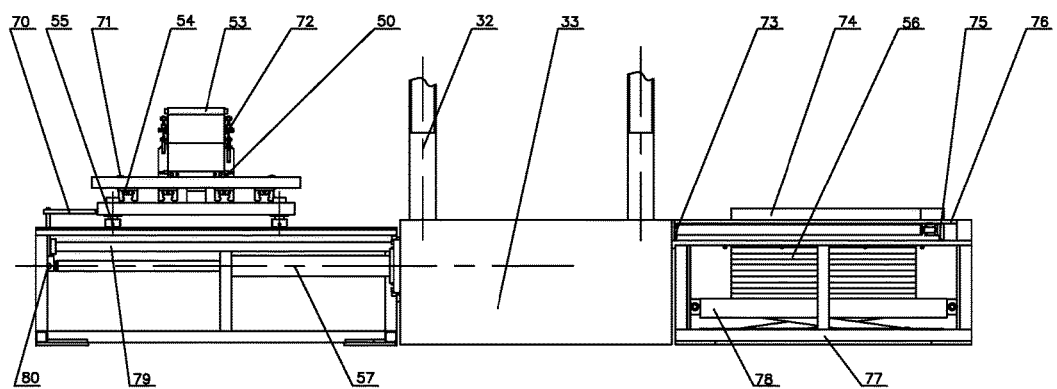
FIG. 10 is a right view of the sample installation and lifting table.
Figure 11:
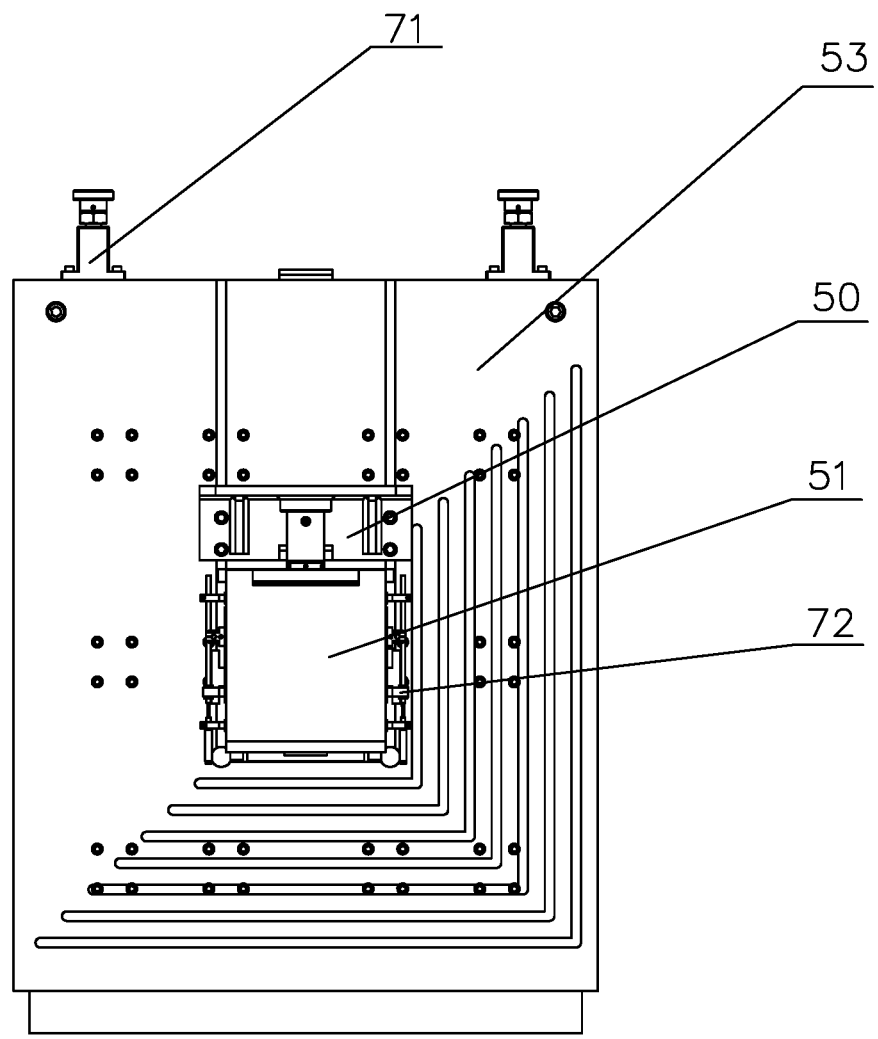
FIG. 11 is a top view of a sample mounting plate of the sample installation and lifting table.
Figure 12:
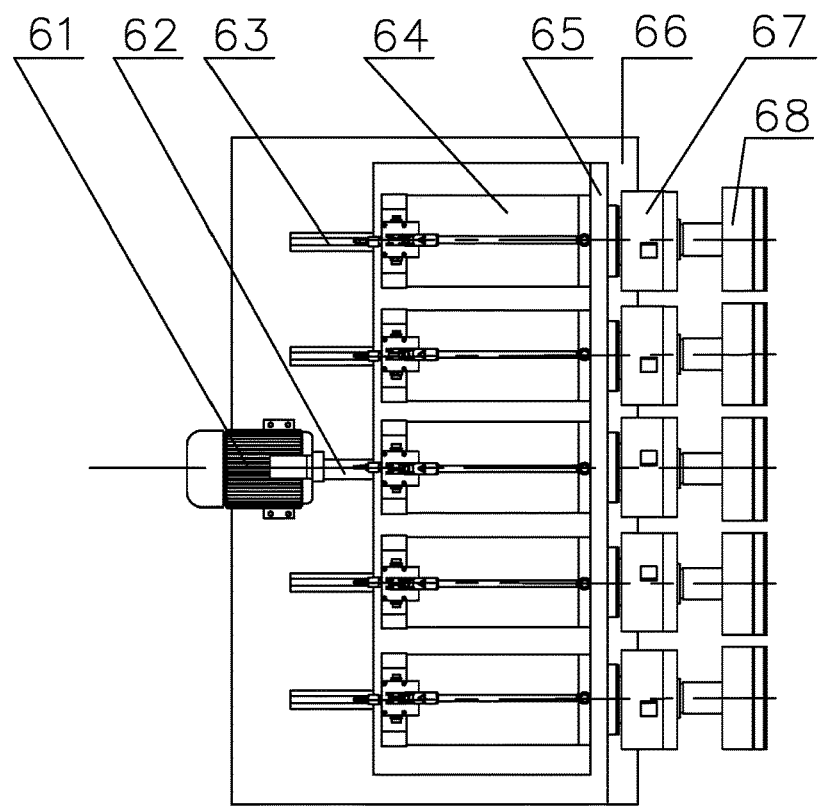
FIG. 12 is a top view of a horizontal loading mechanism.
Figure 13:
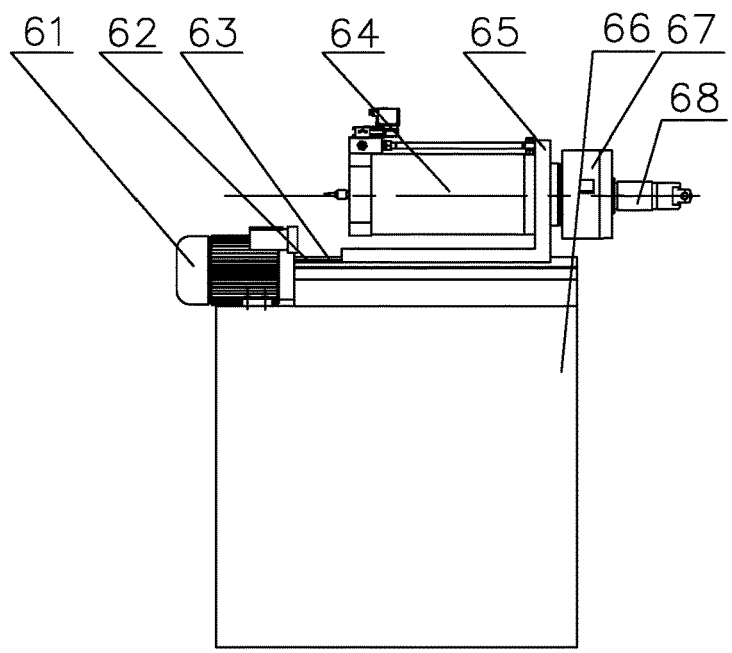
FIG. 13 is a front view of the horizontal loading mechanism.

The trolley 55 is provided with four wheels which can move along the limiting grooves on the two sides of the sample transmission rack 59, and the L-shaped plates 52, the tangential guide rails 54 and the sample mounting plate 53 are placed on the upper portion of the trolley 55, and the L-shaped plates 52 are diagonally mounted on the upper and lower portions of the sample respectively, referring to FIG. 9. A row of the limiting grooves and positioning holes are formed on the sample mounting plate 53 for the purpose of placing the sample and the L-shaped plates on the sample mounting plate 53 and then locking them by the limiting plate from the right side. The sample is tightly pressed by the sample limiting seat 50 from the left side along the grooves and then fixed. The sample loading plate 51 is placed on the L-shaped plate 52 on the upper portion of the sample. The two-stage telescopic cylinder 57 is retracted, so that the supporting rod 70 pushes the trolley 55 onto the platform 33 of the frame 3, and the wheels of the trolley 55 are retracted. The trolley 55 is lifted up by the four lifting hydraulic cylinders 58 to a certain height (a certain height of the kerfs of the sample), and according to the scale of the sample, a certain number of backing plates 56 are lifted up by the lifting table 78 and passed through the backing plate frame 74 to reach a desired height. The backing plate thrust hydraulic cylinders 73 are retracted to convey, by the thrust bars 75, the backing plate frame 74 and the backing plates 56 passing through the backing plate frame 74 to a position right under the trolley 55. The four lifting hydraulic cylinders 58 are descended so that the bottom of the trolley is in proximity to a position right above the uppermost backing plate 56. The piston rods of the four lifting hydraulic cylinders 58 are then fully retracted to the initial position.

According to the requirements on the sample loads, a corresponding force transducer is selected by the horizontal supporting and force measuring mechanism 2. The first force transducer 24 is used for a large sample and a large load. By the jack 202, the height of the first force transducer 24 is adjusted and the supporting rod is mounted. For a small sample, the second force transducer 20 is used, and the supporting rod is mounted on the horizontal supporting tip 21 and then the second force transducer 20 is mounted. The guide rods are locked by the snap rings 26 after the supporting hydraulic cylinder 27 is stretched out in place. Thus, the side edge of the lower sample is resisted by the force transducer for testing.

A certain number of vertical loading actuators and the loading plates are selected to be loaded, according to the scale and load of the sample. Before loading, the sample loading plate 51 and the loading plates 18 are connected by a long soft rope to prevent the sample loading plate 51 from falling down. When a group of vertical loading actuators are loaded to a set load, a certain number of tangential loading actuators 64 and shearing tips 68 are selected to be loaded. When the test is finished, an end of the limiting rod 71, which is mounted on the left side of the sample mounting plate 53, is stretched out by means of thread driving to resist against the fixed bracket 66, so as to prevent the sample mounting plate 53 from moving. For a large sample, the sample will be returned back to the initial position by the supporting hydraulic cylinder 27 and the horizontal supporting tip 21 of the horizontal supporting and force measuring mechanism 2; and for a small sample, the sample may be returned to the initial position manually and by auxiliary tools. Now, the test is finished.

The invention claimed is:

1. A tester assembled by multiple sets of mechanisms for shear strength-scale effect of a rock joint, comprising a frame, a horizontal loading mechanism, a horizontal supporting and force-measuring mechanism, a vertical loading mechanism, and a sample installation and lifting table configured to place different size sample of rock joint;

wherein the horizontal loading mechanism, the horizontal supporting and force-measuring mechanism and the sample installation and lifting table are mounted on a platform on the bottom of the frame, the horizontal loading mechanism and the horizontal supporting and force-measuring mechanism are respectively located on two sides of the sample installation and lifting table; rock joint sample is divided into an upper portion and a lower portion by a slit, the horizontal loading mechanism is configured to load the upper portion of the multi-scale rock joint sample, and the horizontal supporting and force-measuring mechanism is configured to support the lower portion of the multi-scale rock joint sample; the vertical loading mechanism is located above the multi-scale rock joint sample, and can be mounted on the frame in a manner of being movable up and down; and wherein the horizontal loading mechanism comprises at least two tangential actuators, and the vertical loading mechanism comprises a vertical actuator group comprising at least two vertical actuators.

2. The tester assembled by multiple sets of mechanisms for shear strength-scale effect of a rock joint according to claim 1, characterized in that the horizontal supporting and force-measuring mechanism comprises at least two force transducers which are arranged up and down.

3. The tester assembled by multiple sets of mechanisms for shear strength-scale effect of a rock joint according to claim 2, characterized in that the horizontal supporting and force-measuring mechanism comprises a second horizontal force transducer, a horizontal supporting tip, guide rods, a first guide base, a first force transducer, a second guide base, snap rings, a supporting hydraulic cylinder, a mounting frame, guide rods, a linear bearing, a jack and a pedestal; the mounting frame is divided into three layers in vertical direction; the four guide rods, bottoms of which are mounted on the pedestal, are mounted on two sides of a bottom layer of the mounting frame through a linear bearing; and the jack, an acting end of which is connected to the bottom of the mounting frame, is mounted in a middle layer of the mounting frame;

the first force transducer is mounted in the middle layer of the mounting frame; and the supporting hydraulic cylinder is mounted in a top layer of the mounting frame; the piston rod and the horizontal supporting tip are fixed; the horizontal supporting tip, pushed by the supporting hydraulic cylinder, can be used for returning a sample of the upper portion to the original position after the test; and a connecting rod is mounted at a front end of the horizontal supporting tip for mounting the second force transducer.

4. The tester assembled by multiple sets of mechanisms for shear strength-scale effect of a rock joint according to claim 3, characterized in that the guide rods, which pass through the first guide base and the second guide base fixed on the mounting frame, are mounted on two sides of the horizontal supporting tip; and several groups of shaft shoulders which, after moving to a certain position, are sleeved to two sides of the second guide base through the two snap rings for the purpose of limiting the guide rods, are arranged on tail ends of the guide rods.

5. The tester assembled by multiple sets of mechanisms for shear strength-scale effect of a rock joint according to claim 2, characterized in that the vertical loading mechanism comprises a movable beam, vertical actuators, a sprocket drive mechanism, a motor, a vertical force transducer, a movable joint, loading plates and guide rail blocks; worm gears, outer rings of which can be rotatably sleeved inside mounting holes of the movable beam, are provided on two sides of the movable beam, and four upright columns of the frame pass through the worm gears and are in thread fit with inner rings of the worm gears; the sprocket drive mechanism is respectively connected to the motor and a shaft end of a worm, and the worm is meshed with the worm gears, and the motor rotates to drive the worm gears to rotate so that the movable beam moves up and down along the upright columns; an actuator group, comprising 2n+1 actuators distributed symmetrically, is arranged on the movable beam, where n is a natural number; the vertical force transducer, the other end of which is connected to the movable joint, is mounted on a piston rod of each vertical actuator, and the movable joint is connected to the loading plate having a group of guide rail blocks mounted on its bottom.

6. The tester assembled by multiple sets of mechanisms for shear strength-scale effect of a rock joint according to claim 2, characterized in that the frame comprises a fixed beam, upright columns and a platform; the frame is a four-column mechanism; and the four upright columns are mounted on two sides of the platform and the fixed beam, the fixed beam is located above the upright columns, the platform is located below the upright columns, and the upright columns have trapezoidal threads on the upper half thereof.

7. The tester assembled by multiple sets of mechanisms for shear strength-scale effect of a rock joint according to claim 2, characterized in that the sample installation and lifting table comprises a sample limiting seat, a sample loading plate, L-shaped plates, a sample mounting plate, tangential guide rails, a trolley, a two-stage telescopic cylinder, lifting hydraulic cylinders, a sample transmission rack and a supporting rod; the L-shaped plates are diagonally mounted on the upper and lower portions of the sample, respectively, the sample is mounted on the sample mounting plate and limited by the sample limiting seat, the tangential guide rail is mounted on the trolley, and the sample mounting plate is mounted on the tangential guide rail; the sample transmission rack is mounted on one side of the platform of the frame, the two-stage telescopic cylinder is mounted inside the platform, and the supporting tip, on which the supporting rod is mounted, is mounted on the piston rod of the two-stage telescopic cylinder; and the trolley is provided with four wheels which are fixed on a small short-range hydraulic cylinder and move along limiting grooves on two sides of the sample transmission rack, the supporting rod is connected to the trolley, and an acting end of the lifting hydraulic cylinder is located below the trolley and the sample mounting plate.

8. The tester assembled by multiple sets of mechanisms for shear strength-scale effect of a rock joint according to claim 2, characterized in that the horizontal shearing mechanism comprises a tangential motor, a screw rod, dovetail groove sliding tables, tangential actuators, a moving plate, a fixed bracket, horizontal force transducers and shearing tips; at least two tangential actuators distributed symmetrically are mounted on the moving plate; the moving plate and the fixed bracket are connected by a group of dovetail groove sliding tables; a screw rod mounting base connected to the screw rod is mounted on the bottom of the moving plate, and one end of the screw rod is connected to the tangential motor; and the horizontal force transducer, on which the shearing tips are mounted, is mounted on the piston rod of each tangential actuator.

9. The tester assembled by multiple sets of mechanisms for shear strength-scale effect of a rock joint according to claim 1, characterized in that the vertical loading mechanism comprises a movable beam, vertical actuators, a sprocket drive mechanism, a motor, a vertical force transducer, a movable joint, loading plates and guide rail blocks; worm gears, outer rings of which can be rotatably sleeved inside mounting holes of the movable beam, are provided on two sides of the movable beam, and four upright columns of the frame pass through the worm gears and are in thread fit with inner rings of the worm gears; the sprocket drive mechanism is respectively connected to the motor and a shaft end of a worm, and the worm is meshed with the worm gears, and the motor rotates to drive the worm gears to rotate so that the movable beam moves up and down along the upright columns; an actuator group, comprising 2n+1 actuators distributed symmetrically, is arranged on the movable beam, where n is a natural number; the vertical force transducer, the other end of which is connected to the movable joint, is mounted on a piston rod of each vertical actuator, and the movable joint is connected to the loading plate having a group of guide rail blocks mounted on its bottom.

10. The tester assembled by multiple sets of mechanisms for shear strength-scale effect of a rock joint according to claim 9, characterized in that, in the vertical loading mechanism, the 2n+1 vertical actuators are distributed in a shape of "-" or "X".

11. The tester assembled by multiple sets of mechanisms for shear strength-scale effect of a rock joint according to claim 1, characterized in that the frame comprises a fixed beam, upright columns and a platform; the frame is a four-column mechanism; and the four upright columns are mounted on two sides of the platform and the fixed beam, the fixed beam is located above the upright columns, the platform is located below the upright columns, and the upright columns have trapezoidal threads on the upper half thereof.

12. The tester assembled by multiple sets of mechanisms for shear strength-scale effect of a rock joint according to claim 1, characterized in that the sample installation and lifting table comprises a sample limiting seat, a sample loading plate, L-shaped plates, a sample mounting plate, tangential guide rails, a trolley, a two-stage telescopic cylinder, lifting hydraulic cylinders, a sample transmission rack and a supporting rod; the L-shaped plates are diagonally mounted on the upper and lower portions of the sample, respectively, the sample is mounted on the sample mounting plate and limited by the sample limiting seat, the tangential guide rail is mounted on the trolley, and the sample mounting plate is mounted on the tangential guide rail; the sample transmission rack is mounted on one side of the platform of the frame, the two-stage telescopic cylinder is mounted inside the platform, and the supporting tip, on which the supporting rod is mounted, is mounted on the piston rod of the two-stage telescopic cylinder; and the trolley is provided with four wheels which are fixed on a small short-range hydraulic cylinder and move along limiting grooves on two sides of the sample transmission rack, the supporting rod is connected to the trolley, and an acting end of the lifting hydraulic cylinder is located below the trolley and the sample mounting plate.

13. The tester assembled by multiple sets of mechanisms for shear strength-scale effect of a rock joint according to claim 12, characterized in that the sample installation and lifting table further comprises backing plates, backing plate thrust hydraulic cylinders, a backing plate frame, thrust bars, guide bars, a backing plate transmission rack, a lifting table, guide rods and a supporting tip; a set number of backing plates are amounted according to the scale of the sample so that kerfs of the sample are on a same level of height; the backing plate transmission rack is mounted on the other side of the platform of the frame; one backing plate lifting table, on which the backing plates are mounted, is mounted inside the backing plate transmission rack; the backing plate thrust hydraulic cylinders are respectively mounted on two sides of the other side of the platform, and the thrust bars are mounted on the piston rods of the two backing plate thrust hydraulic cylinders; the backing plate frame fixed to the thrust bars is located right above the backing plates, and the two sides of the backing plate frame are movably mounted on the guide bars of the backing plate transmission rack.

14. The tester assembled by multiple sets of mechanisms for shear strength-scale effect of a rock joint according to claim 1, characterized in that the horizontal shearing mechanism comprises a tangential motor, a screw rod, dovetail groove sliding tables, tangential actuators, a moving plate, a fixed bracket, horizontal force transducers and shearing tips; at least two tangential actuators distributed symmetrically are mounted on the moving plate; the moving plate and the fixed bracket are connected by a group of dovetail groove sliding tables; a screw rod mounting base connected to the screw rod is mounted on the bottom of the moving plate, and one end of the screw rod is connected to the tangential motor; and the horizontal force transducer, on which the shearing tips are mounted, is mounted on the piston rod of each tangential actuator.

\* \* \* \* \*